United States Patent [19]

Viertl

[11] Patent Number: 5,334,934
[45] Date of Patent: Aug. 2, 1994

[54] EDDY CURRENT PROBE APPARATUS AND INTERLACED SCANNING METHOD FOR INTERIOR INSPECTION OF METAL DEVICES

[75] Inventor: John R. M. Viertl, Niskayuna, N.Y.

[73] Assignee: General Electric Company, Schenectady, N.Y.

[21] Appl. No.: 999,650

[22] Filed: Dec. 31, 1992

Related U.S. Application Data

[63] Continuation-in-part of Ser. No. 729,725, Jul. 15, 1991.

[51] Int. Cl.$^5$ .............. G01N 27/72; G01N 27/82; G01B 33/12
[52] U.S. Cl. ...................... 324/220; 324/262
[58] Field of Search .............. 324/243, 242, 237, 238, 324/219, 220, 221, 261, 262, 225

[56] References Cited

U.S. PATENT DOCUMENTS

| | | | |
|---|---|---|---|
| 3,582,771 | 1/1971 | Placke | 324/226 |
| 4,134,067 | 1/1979 | Woodbury | 324/219 |
| 4,258,319 | 3/1981 | Shimada et al. | 324/226 |
| 4,755,753 | 7/1988 | Chern | 324/237 |

Primary Examiner—Walter E. Snow
Attorney, Agent, or Firm—Nixon & Vanderhye

[57] ABSTRACT

A method and apparatus for metal flaw detection using multiple eddy current probes contained in a single carriage. An interlaced scanning method allows the scanning line spacing to be narrower than the spacing between probes on the probe carriage. The probes are held at a constant lift-off distance from the surface by a probe carriage that slides across the surface in a straight scan line. The probe carriage moves relative to a motorized bracket that slides the carriage across the surface.

8 Claims, 8 Drawing Sheets

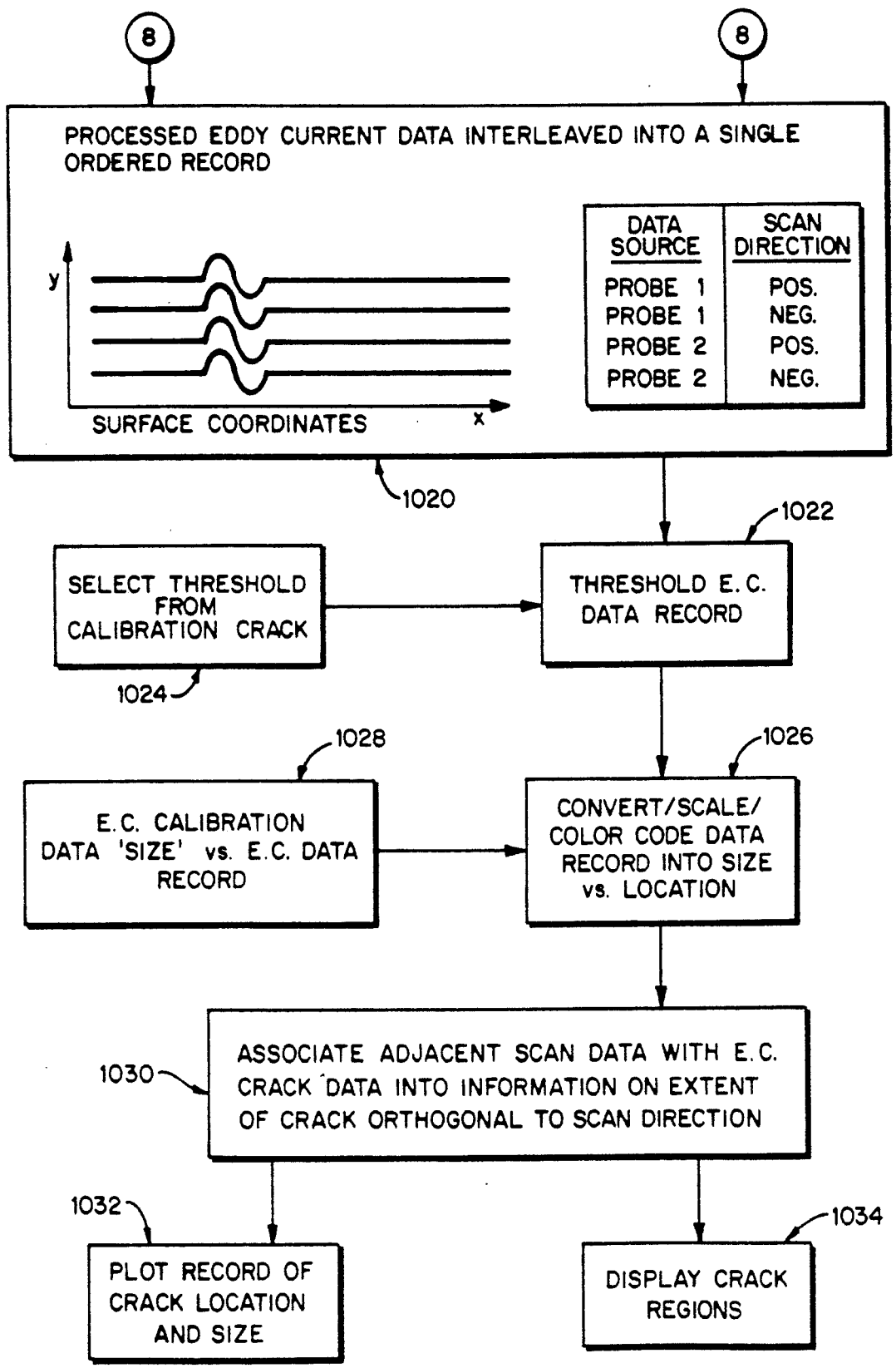

EDDY CURRENT PROBE APPARATUS AND INTERLACED SCANNING METHOD FOR INTERIOR INSPECTION OF METAL DEVICES

This application is a continuation-in-part of U.S. application Ser. No. 07/729,725, filed Jul. 15, 1991, and which is incorporated by reference.

FIELD OF THE INVENTION

This application relates to eddy current probes for detecting flaws in conductive materials or semiconductive materials and, in particular, to scanning methods using eddy current probes for detecting flaws in retaining rings for electromagnetic generators.

BACKGROUND AND SUMMARY OF THE INVENTION

Eddy currents provide a measurable indicator of flaws in the surface and sub-surface of conductive materials. They are generally confined to the surface and near surface regions of the material. They are affected by changes in the resistivity of the conductive material. Flaws in the material, such as microscopic hair line cracks or pits, affect the localized resistivity of the material. Flaws in a material cause localized variations in the eddy currents in the material. Accordingly, a conductive material can be inspected for flaws by inducing and measuring eddy currents in the material.

Eddy current probes detect material flaws by sensing variations in eddy currents. These probes have coils with high frequency currents that project a fluctuating magnetic field into the conductive material being measured. This imposed magnetic field induces eddy currents in the material. The strength of the eddy currents depends on the local resistivity of the material which resistivity is affected by the presence of material flaws and cracks. The eddy currents create a magnetic field that varies in intensity with the strength of the eddy current and, hence, the presence of material flaws.

The magnetic field created by the eddy currents extends above the material surface up to the probe. The magnetic field from the eddy current induces its own voltage in the probe coil. The eddy magnetic field opposes the coil field. These coupled magnetic fields measurably influence the net current and inductance of the probe coils. These variations in the coil currents vary in response to material flaws are measured to detect these flaws.

For the probe coil current to reliably indicate variations in eddy currents, other parameters that affect the coil current must be held constant. One such parameter is the distance between the face of the probe and the surface of the material. The degree of coupling between the magnetic fields from the coil current and the eddy current depends on the gap between the probe and the material with the eddy currents. The gap between the probe and material is known in the art as being the "lift-off" of the probe.

Changes in the lift-off gap alter the amount of magnetic coupling and the coil current in the eddy current probe. An eddy current probe is influenced by current alterations due to gap changes as it is influenced by current variations due to material flaws. Since it is desired to detect only eddy current variations due to material flaws, current variations due to changes in the lift-off gap must be segregated from variations clue to material flaws.

It is difficult to maintain a constant gap distance between the probe and the material being tested. It is particularly difficult to maintain a constant gap when a large surface, such as a retaining ring for a power generator, is being tested. Retaining rings are large and typically have radii in the range of 13 to 36 inches.

Retaining rings are not perfect cylinders, because they are large and their surfaces have been reworked from earlier maintenance. During the Life of a retaining ring, it may be removed several times from the generator rotor shaft for reworking. Each time a retaining ring is reinserted onto the generator shaft by shrink fitting, the ring deforms slightly to conform to the slotted surface of the rotor. Accordingly, the surface of the retaining ring becomes more irregular each time the ring is reworked.

The surface of a retaining ring is immense compared to the small material flaws that an eddy current probe detects. Large retaining rings do not have surfaces that are uniform at the small order of magnitude (microcracks) at which the eddy currents are being measured. The irregularities in the shape and surface of the retaining ring make it difficult to hold the probe a constant distance above the surface of tile ring.

Eddy current probes are usually fixed with respect to a known reference other than the retaining ring. A true and known reference is necessary to precisely position the probe with respect to the retaining ring. The retaining ring usually bears a stamp on its end surface marking the zero degree position of the ring. The position the eddy current probe is referenced from this zero reference stamp. A reference for the probe is established with a conventional reference frame. This reference frame is attached to the retaining ring and is centered on the axis of the ring as shown in FIG. 1. The eddy current probe is affixed to the reference frame and positioned near the surface of the retaining ring. The reference frame is motorized so that the eddy current probe can be drawn across the surface of the retaining ring. Generally, the probe is moved axially along the length of the retaining ring in a straight scan line.

As the probe completely traverses each scan line across the retaining ring surface, the probe is circumferentially indexed to the next scan line around the reference frame. The probe is then drawn in reverse along this next scan line. This scanning and indexing sequence is repeated until the probe completely scans the entire circumference of the retaining ring. In this way, the probe covers the entire surface of the retaining ring. The probe must cover the entire ring to ensure that all material flaws are detected. To do this, the probe travels along straight scan lines parallel to the axis of the retaining ring. If the probe wanders off a scan line, then portions of the material surface will be missed by the probe and flaws in the material may escape detection. Moreover, it is difficult to accurately specify the location of flaws when the probe drifts off the intended scan line.

Prior to the present invention, eddy current probes generally scanned a retaining ring with a single probe one scan line at a time. This prior scanning method was inordinately slow because the one probe had to cover the entire retaining ring. The one line at a time scanning method was previously believed to be the only method suited for scanning retaining rings and other applications where the probe was rotated about a stationary surface.

The use of multiple probes in a single carriage was known for eddy current scanning where the surface rotated relative to the probe. For example, U.S. Pat. No. 4,258,319 discloses a carriage with a plurality of eddy current probes that scan a rotating shaft. However, the use of multiple probes was previously limited to scanning outside rotating surfaces because of complex and bulky carriages that carried the probe. Accordingly, a long-felt need existed for faster methods of scanning the interior surfaces of retaining rings with eddy current probes.

In the present invention, a carriage holds a plurality of eddy current probes held a fixed distance above the retaining ring surface. The carriage has self-lubricating feet that slide across the surface of a retaining ring. The carriage moves in a straight line along the surface of the retaining ring. As the carriage moves, the eddy current probes trace a plurality of parallel scan lines across the surface of the retaining ring. The probes in the carriage are usually separated by a distance greater than the desired distance between scan lines. This separation of probe is necessary to prevent cross-talk between the electromagnetic fields of the probes, and due to the size of the probes and probe mounting of the carriage. A novel scanning method was required to achieve the desired narrow spacing of scan lines with a multiple probe carriage.

In operation, once the probe carriage traverses the ring surface in one direction, the carriage is shifted incrementally sideways by a distance equal to the width of the row of probes held in the carriage. The carriage then traverses the surface in an opposite direction. By shifting sideways the carriage and scanning the ring surface back and forth, the carriage and probes cover the entire surface of the retaining ring. However, the distance between scan lines after one rotation of the carriage around the retaining ring is the distance separating the probes on the carriage to achieve finer spacing of scan lines, the carriage must rotate around the retaining ring more than once.

When the probe carriage begins the second rotation around the retaining ring, the probes scan lines that are interlaced between the scanned lines of the prior carriage rotation. By interlacing scan lines, the distance between scan lines is less than the distance between the probes on the carriage. By reducing the distance between scan lines, the ability of the eddy current instrument to detect small cracks and flaws in a material is enhanced.

Some signal noise will be present in the coil current. It is not practical to mechanically eliminate all of the sources of signal noise. Accordingly, signal processing techniques are used to discriminate the current signals attributable to variations in the eddy current from noise and other undesirable signals. The principal signal processing technique employed in the present invention is to compare two coil signals that are nearly identical but for the desired eddy current signal. A split coil eddy current probe provides these two similar current signals.

Both coils have the same drive current and are drawn along adjacent parallel paths over the surface of the retaining ring. Both coils are magnetically coupled to the eddy currents that they each separately induce into the retaining ring surface. The gap between the ring surface and the probe is the same for both coils. Accordingly, the coil currents for each coil are substantially the same.

The two coils are far enough apart so that they will not pass over the same material flaws in the ring surface at the same time. Although the coils within each probe are side by side and very close together, they do not project overlapping magnetic fields onto the same portion of the ring surface. The magnetic fields generated by the each of coils and projected against the ring surface has a shape substantially the same as that of the end of the coil. The side-by-side coils project side by side magnetic fields onto the ring surface.

Since the flaws in the retaining ring material tend to be microscopic, individual flaws generally do not traverse across the side-by-side magnetic fields. When one probe coil passes over a particular feature of a material flaw, the other coil does not pass over the same flaw feature. Since material flaws affect the eddy currents that magnetically couple a coil, the current in the coil passing over the flaw is affected by the altered eddy current while the other coil current is not affected by the flaw. Accordingly, the difference between the two coil current signals is due to microflaws in the ring surface and sub-surface.

In addition, most of the noise and other signal effects in the eddy current probe can be masked from the coil signal by using impedance bridge and amplifier circuits to process the coil current signals. These circuits are contained in a conventional eddy current instrument such as an MIZ-40 model instrument manufactured by the Zetec Corp. of Issaquah, Washington. Similarly, it is acceptable to use two or more single probe channel instruments such as a model 19E, Phase II, instrument manufactured by Stanley NDJ Technologies, Inc., Kennewick, Washington, and modified for wide band width operation.

To further refine the signals from the eddy current probe, the coil signals from the bridge circuit are passed through two synchronous differential amplifier circuits to create two difference signals. One amplifier is synchronized with the drive oscillator. The in-phase signal, after the addition of a user selectable display phase angle ($\phi$), can be rotated on the display screen so that it generally corresponds to liftoff variations between the two coils (to the extent that such variations exist with side-by-side coils) and other noise.

The second synchronous differential amplifier has a 90° phase shift with the drive oscillator and compares the out-of-phase differences between the coil signals. The out-of-phase signal, after the addition of the same user selectable display phase angle ($\phi$), is rotated on the display or plot so that it generally corresponds to variations in the eddy currents between the two coils and which are due to material flaws. Since the eddy currents are generated by and magnetically coupled to the coil current, the eddy currents are slightly behind the phase of the col 1 current. The eddy currents tend to retard the coil current because of the magnetic coupling. The currents in the two coils will be out-of-phase due to the eddy currents. Accordingly, the out-of-phase signal is more indicative of material flaws than is the in-phase signal.

Signal processors are used to digitize the eddy current signals and to present the signals in a coherent manner to the operators. The signals (in-phase and out-of-phase) from each probe are centered to account for drifting, filtered to eliminate noise, normalized and collated so as to show spatially the size and location of flaws and cracks in the surface of a retaining ring.

The processed signal data from the eddy current probe is displayed via conventional display means. Strip charts have been used to show each scan line of the probe and show where the eddy current varies with respect to the material surface. Similarly, CRT display screens can be used to present the eddy current data. The display may be adjusted to show the in-phase and out-of-phase differential signals on respective horizontal and vertical display axes to enhance the user's ability to analyze the data. In addition, a computer can be used to display the signals, and to color-code and plot the signals for a display or to print a paper copy of the data. The displays have in common the presentation of data indicative of material flaws in the ring. The data may be presented such that the location of the flaws in the material is apparent or may be presented such that the area and extent of the flaws are apparent.

It is an object of the present invention to provide an improved eddy current probe, carriage and signal processor. The carriage holds multiple probes to reduce the time needed to scan a surface. An interlaced straight lined scanning method reduces the distance between scan lines to less than the distance between probes on the carriage. A signal processing technique is used to segregate current variation due to material flaws from current variations due to noise and lift off.

BRIEF DESCRIPTION OF THE DRAWINGS

FIGS. 6 and 8 flowcharts showing the algorithms used to process the eddy current signals.

DETAILED DESCRIPTION OF THE DRAWINGS

Figure 1:
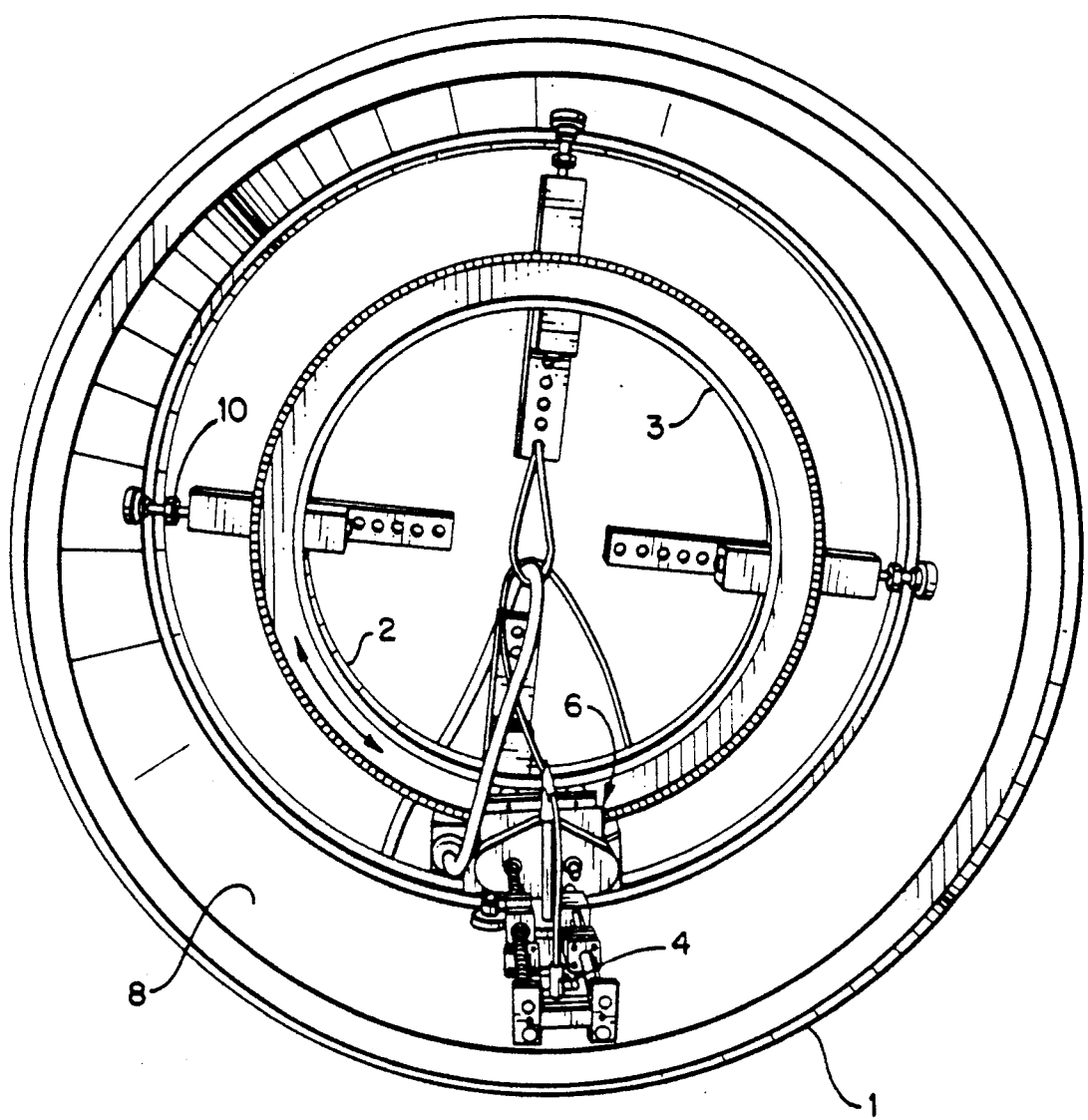
FIG. 1 is an end view of a generator retaining ring in which has been mounted a reference frame, a probe carriage and an eddy current probe.

FIG. 1 shows a retaining ring 1 for a large electric power generator (not shown) in which a reference frame 2 has been coaxially mounted. The retaining ring is substantially cylindrical and composed of a conductive metal in which eddy currents can be induced. The surfaces of the retaining ring are inspected for material flaws before being installed on generator rotors and during periodic reworking of the rotors. This inspection includes using a plurality of eddy current probes 4 mounted in a carriage 6 that are movably fixed to the reference frame 2.

The eddy current probes traverse the entire inner surface 8 of the retaining ring searching for material flaws. The eddy current probes 4 are slid axially in a straight line back and forth across the retaining ring surface by the carriage and motorized reference frame. Each axial pass by each probe across the retaining ring surface generates one straight scan line. After each pass, the carriage is indexed slightly around the circumference of the interior surface (in the direction theta $\theta$) of the retaining ring to position the eddy current probes on another set of scan lines.

The probe scans in both forward and reverse directions. The sequence of scanning the eddy current probe axially along the retaining ring surface and indexing the carriage with respect to the reference frame is repeated until the probes traverse the entire circumferential surface of the retaining ring at least twice. The carriage circles the retaining ring more than once so that the probes interlace prior scan lines during each subsequent pass around the retaining ring. By interlacing the scan lines, the final distance between scan lines can be as small as desired and narrower than the gap between the probes on the carriage. Both the interior and exterior surface of the retaining ring may be inspected by the eddy current probe in this way.

Figure 2:
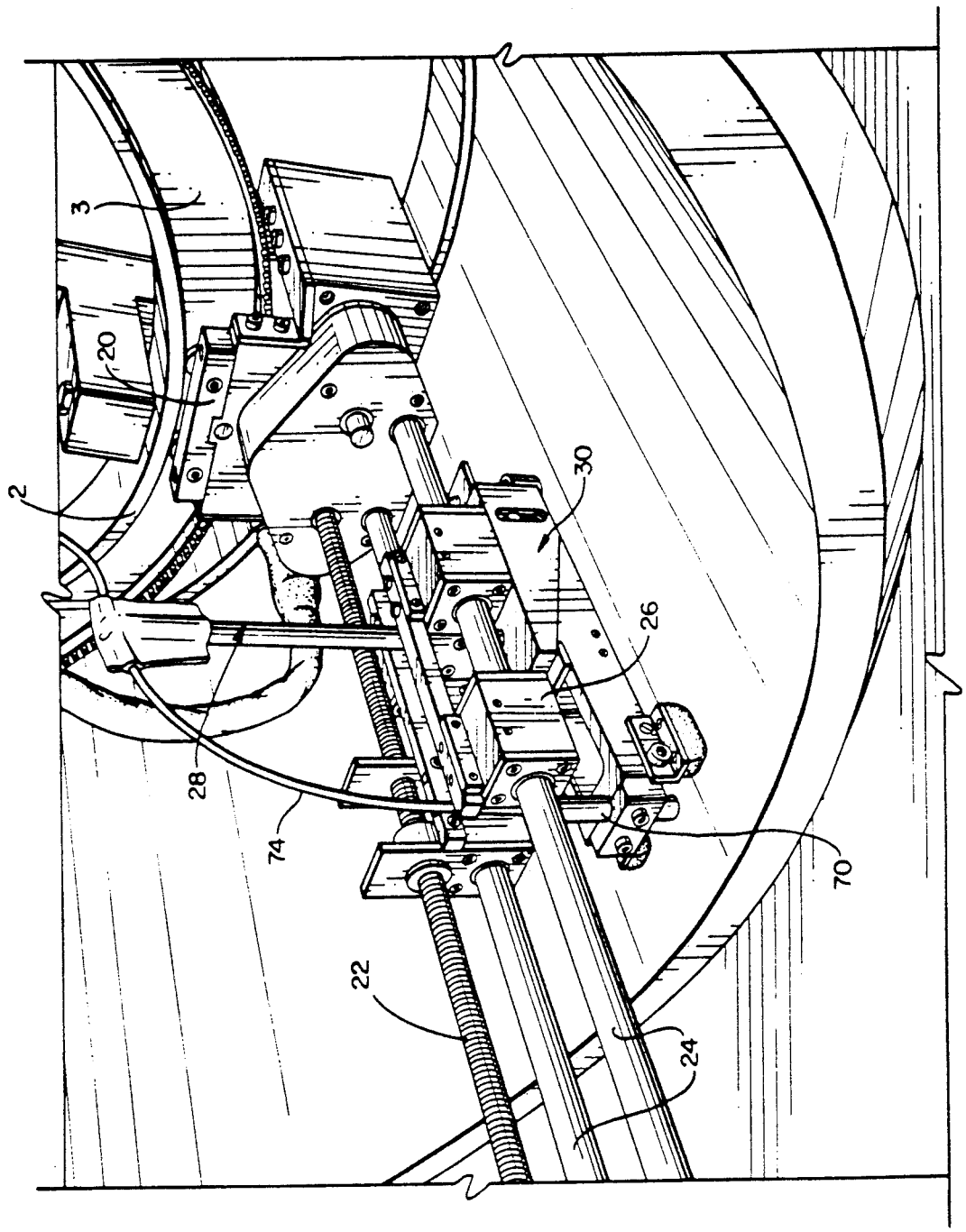
FIG. 2 is a perspective view of a probe carriage mounted on a reference frame in a retaining ring.

As shown in FIG. 2, the reference frame 2 is coaxially aligned with the retaining ring. In the preferred embodiment, the reference frame and a motorized Alara ™ scanner mount 20 are conventional and manufactured by the Virginia Corporation of Richmond, Virginia. A one-probe embodiment of the probe carriage is described in detail in co-pending U.S. application Ser. No. 07/729,725 entitled "Carriage For Eddy Current Probe Having Contact Ball Engagement Between Carriage And Translation Means" which is incorporated by reference. The present embodiment of the carriage has been modified to accommodate two or more probes for multi-probe scanning.

The annular ring of the reference frame has an annular array of teeth that engage a motorized mount 20 as it moves around the annular frame. The engagement of the mount and the teeth allow the mount to be precisely indexed around the annular ring such that the annular position of the mount (and the probe) in the retaining ring can be controlled and determined.

As shown in FIG. 2, the mount includes three shafts that extend above the surface of the retaining ring and are parallel to the ring axis. The first shaft 22 is a threaded shaft that is rotated by the motorized mount. As the threaded shaft rotates it engages a mount bracket 26 and moves the bracket and carriage 30 across the surface of the retaining ring. The other two shafts 24 maintain the alignment of the bracket and carriage. The bracket 26 slides along these parallel alignment shafts in a straight line parallel to the ring axis. The bracket 26 engages a rod 28 which is attached to the probe carriage 30. This rod couples the bracket 26 to the carriage. The movement of the bracket is translated to the carriage by the rod 28. The eddy current probes 70 are firmly held by the carriage and the probes are electrically coupled by cables 74 to the signal processing electronics.

Figure 3:
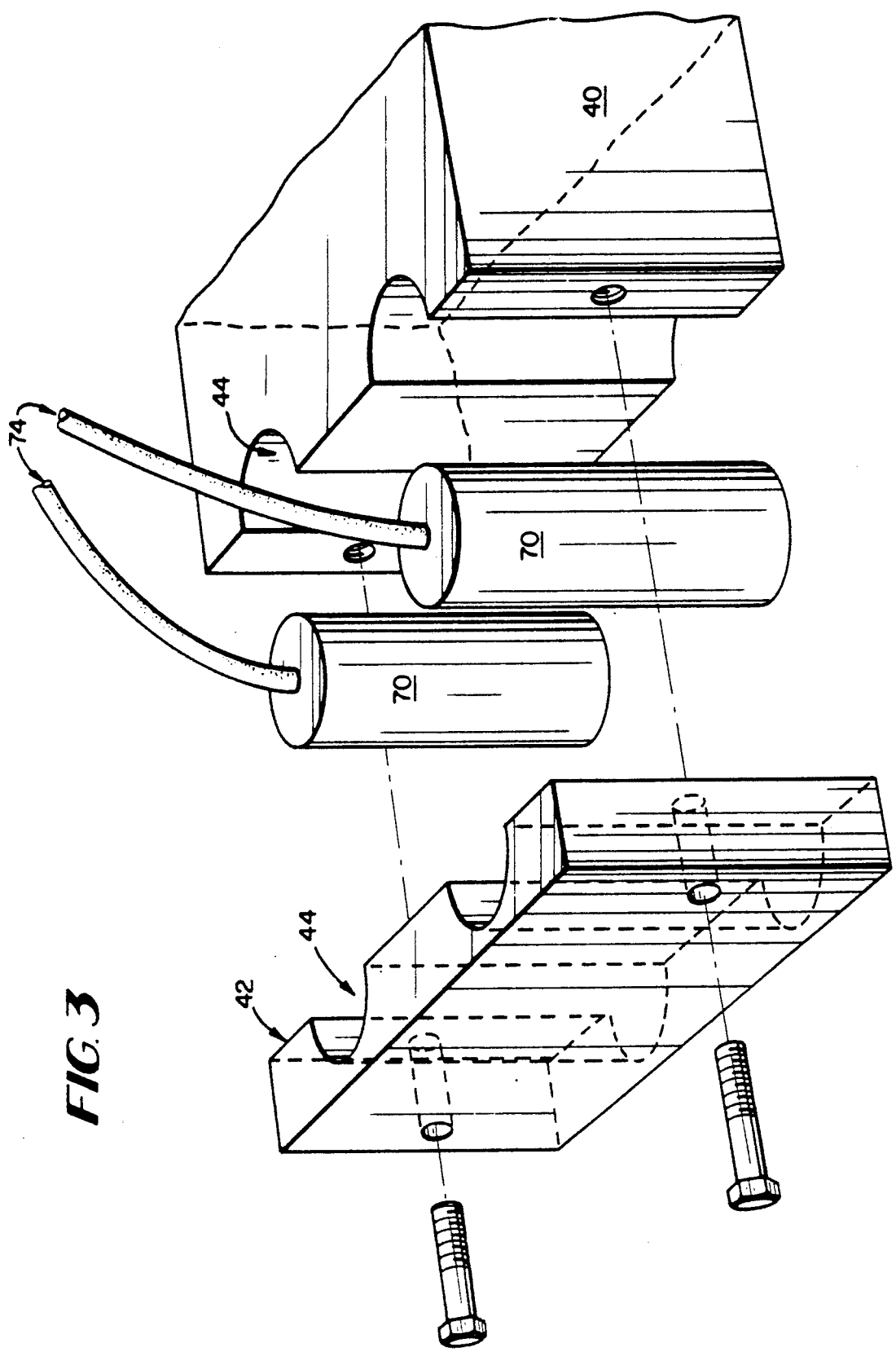
FIG. 3 is an exploded view of a carriage probe mount and two eddy current probes.

FIG. 3 shows a carriage end 40 for mounting a pair of eddy current probes 70. A bracket 42 screws to the end of the carriage to clamp the eddy current probes in place. Hemicylindrical recesses 44 in tile end of the carriage and in the bracket allow the probes to securely seat in the carriage. More than two probes would be mounted on a single carriage in other carriage embodiments.

Figure 4:
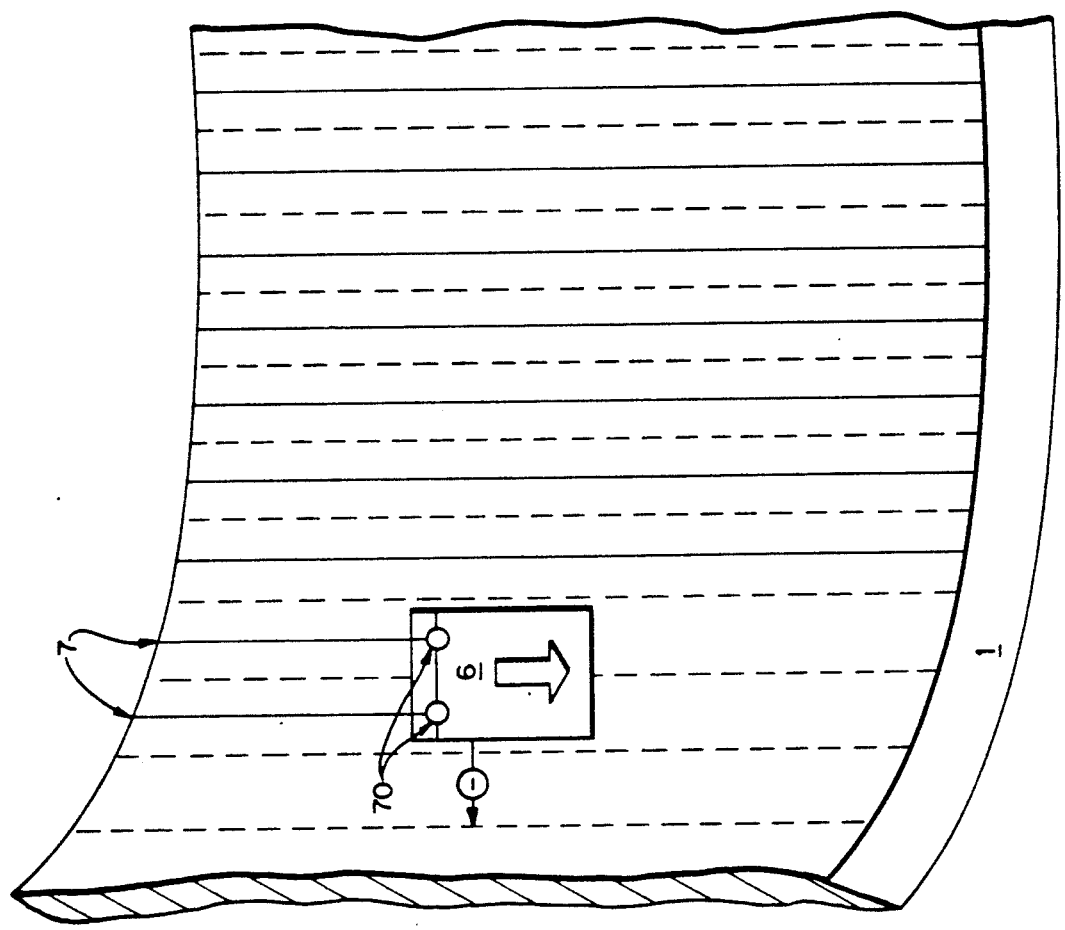
FIG. 4 shows an exemplary set of interlaced scan lines traced by the eddy current probes and carriage.

As shown in FIG. 4, the carriage 6 is moved axially across the inside surface of the retaining ring 1. As the carriage moves, the twin eddy current probes 70 trace a pair of straight scan lines 7 across the ring surface. Eddy current signals are transmitted from the probe to signal processing circuits. The distance between the probes is the distance between the pair of scan lines traced by the carriage.

It is preferable to interlace the scan lines so that the distance between scan lines can be less than the distance between the plurality of probes on the carriage. Interlacing scan lines can be accomplished by twice rotating the carriage about the rotating ring. The second time the carriage rotates around the retaining ring, the carriage is offset by one-half the distance between the first series of scan lines such that the second set of scan lines is interlaced with the first set of scan lines. To achieve even narrower spacing between scan lines, the carriage can be rotated multiple times around the retaining rings. Each time the carriage begins a new rotation about the retaining ring, the carriage is offset in the $\theta$ direction by the desired distance between scan lines. With this scanning method, a multiple probe carriage can be used to achieve very close spacing of scan lines.

Figure 5:
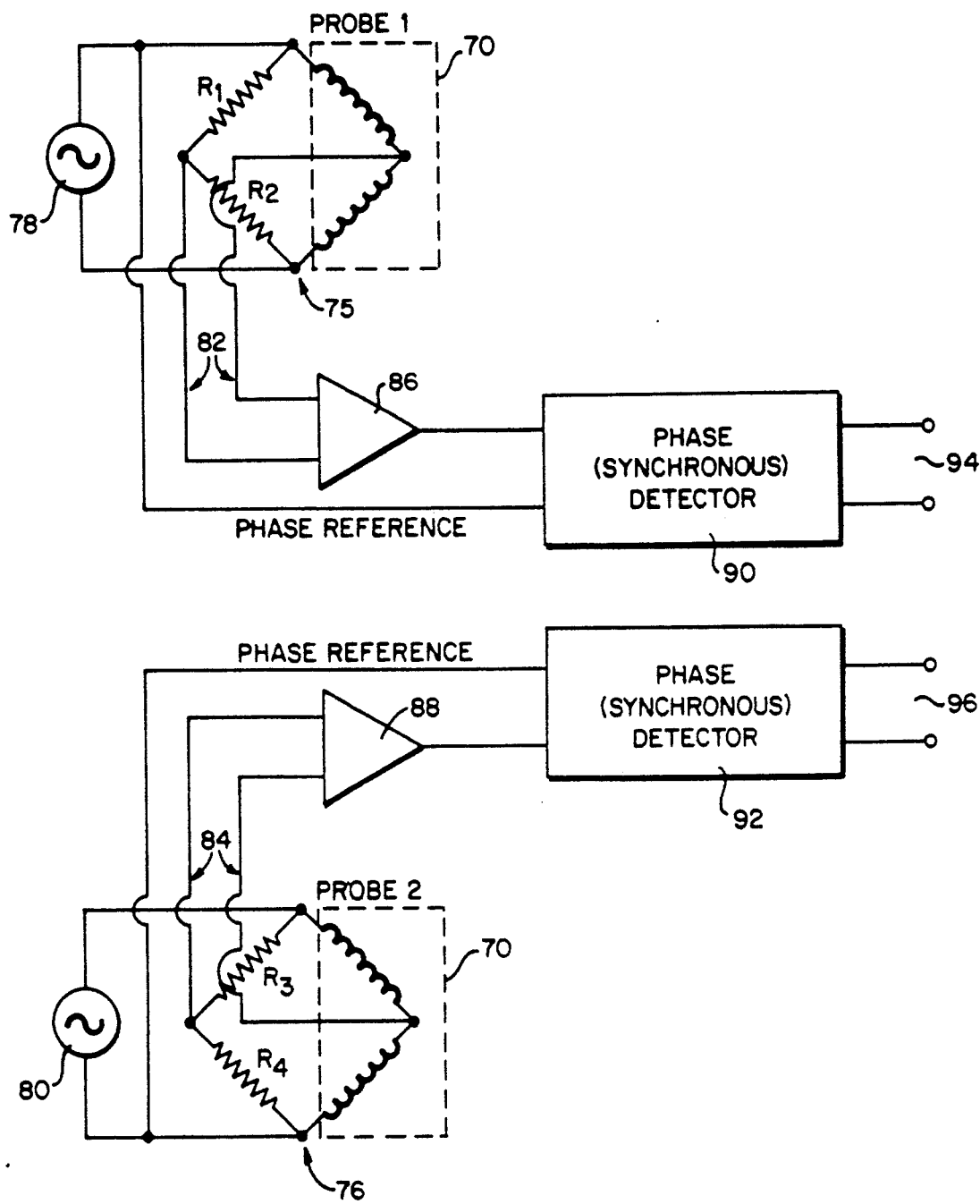
FIG. 5 is a schematic diagram of a portion of the circuitry used to process the eddy current signals.

FIG. 5 shows a schematic circuit diagram of the signal amplifier and phase detector for the eddy current coil signals. Typically, this circuit, with the exception of the probe coils is contained in an eddy current instrument. A signal cable from the probe coil is coupled to the instrument. The pair of wires 74 from each of the two split coils in each probe are coupled to balanced impedance bridge circuits 75, 76. Two of the resistance arms $R_1/R_2$, $R_3/R_4$ of this bridge circuit have identical electrical resistance values and are coupled to drive oscillators 78, 80 that provide the alternating high frequency current for the coils of the eddy current probes. The other two arms of the bridges are coupled to the eddy probe coils. The coils are grounded within the bridge. Accordingly, both coils receive identical oscillating currents through the bridge.

Each bridge detects impedance imbalances between the pair of probe coils. Current signals from the coils are passed through the leads 82, 84 that couple the bridge circuit to the gain amplifiers 86, 88. Two synchronous phase detectors 90, 92 segregate the in-phase and out-of-phase signals into separate channels for each probe signal. The oscillators each provide a phase reference signal to their respective phase detectors. These phase detectors compare the impedance between the two coils and provide difference signals over leads 94, 96 to the data acquisition system.

The data acquisition system processes the raw eddy current signals from the phase (synchronous) detectors. The hardware for the data acquisition system is conventional and may be embodied in a personal computer. To convert the analog probe data into digital form, a Datal Analog-to-Digital converter card is inserted into the PC computer. Datal converter cards are available from the Sonix Corporation of Springfield, Virginia. The data acquisition system is programmed to process the eddy current signals for presentation and analysis by technicians.

Figure 6:
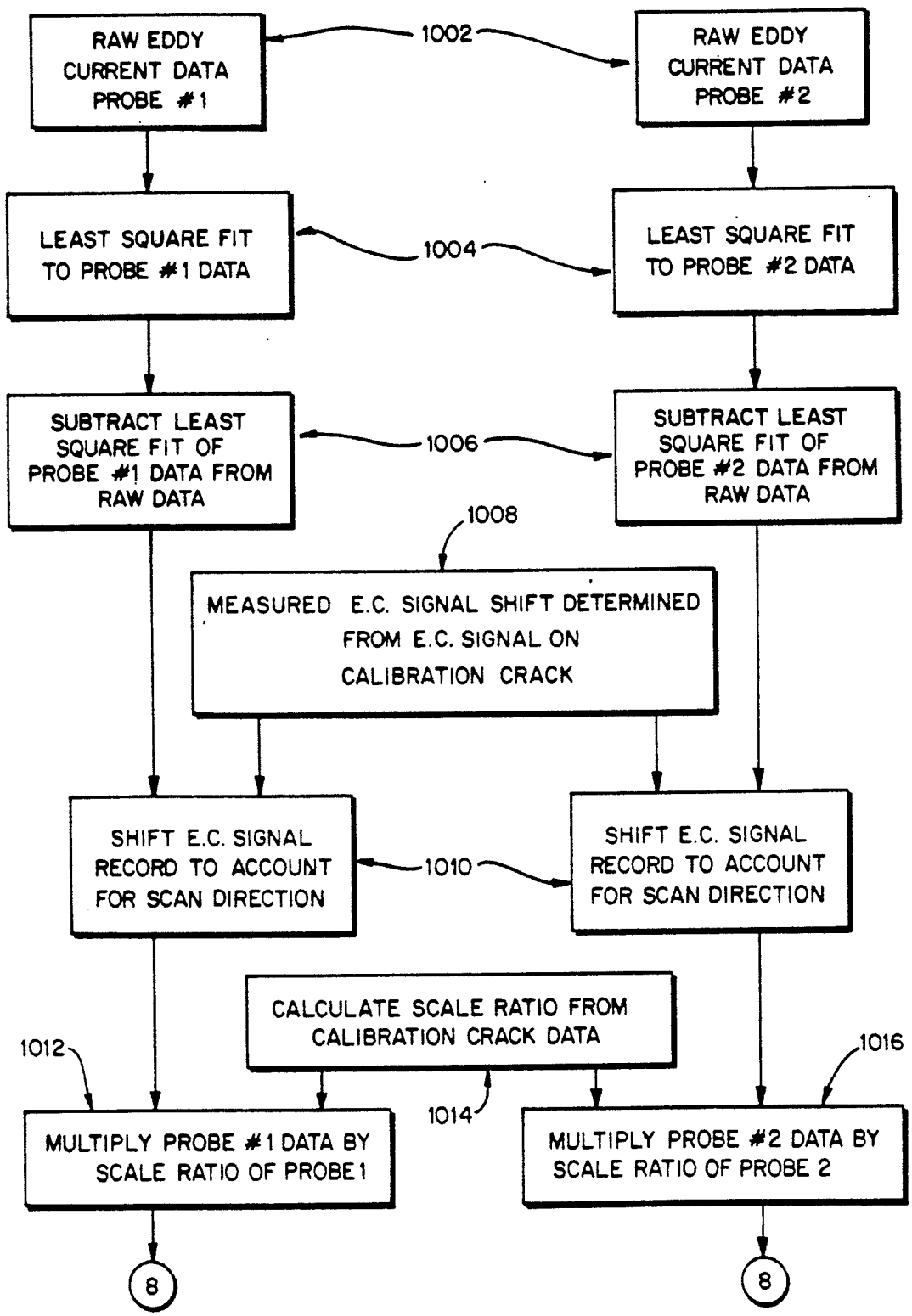
Figure 7A:
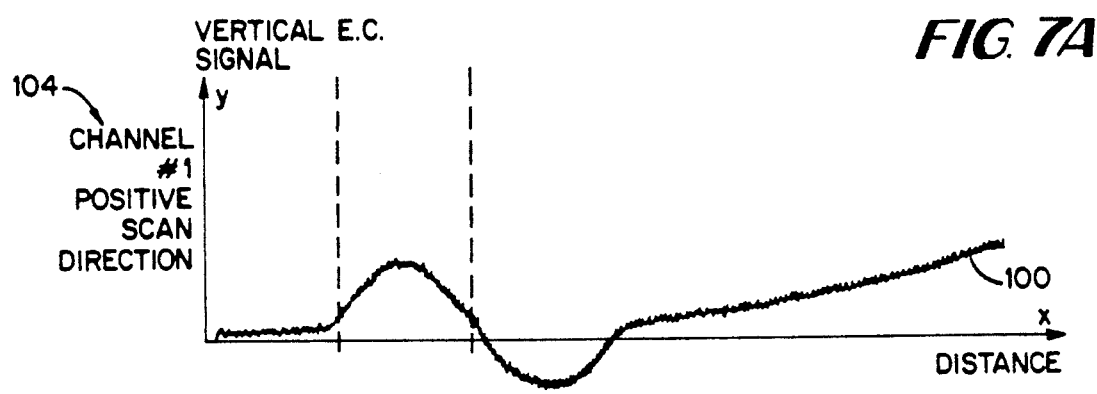
FIGS. 7(A) to 7(D) show exemplary plots of partially processed eddy current signals.
Figure 7B:
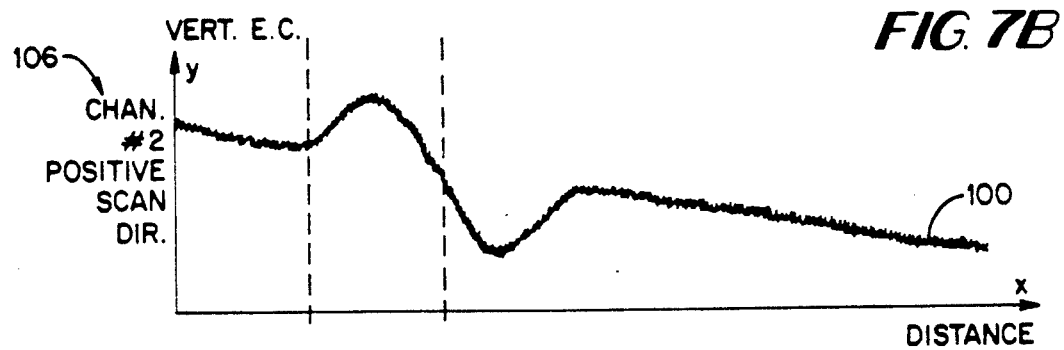
Figure 7C:
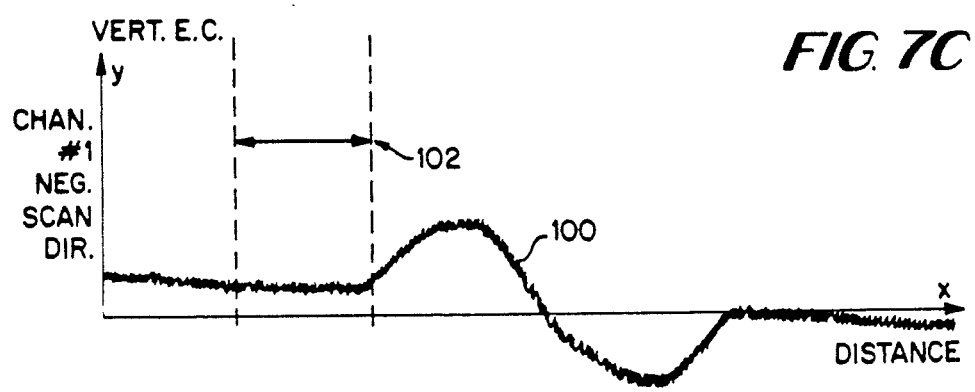
Figure 7D:
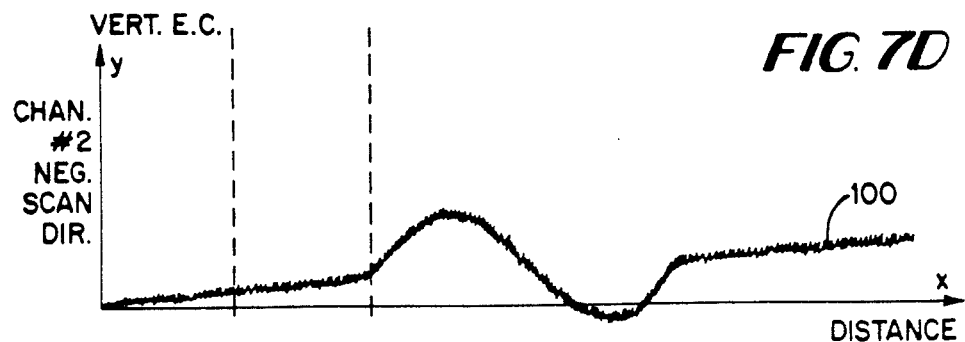

FIG. 6 provides a computer software flow chart for the processing of the raw eddy current signals. At step 1002, the raw eddy current data from each probe is received and digitized by the data acquisition system. FIGS. 7(A) to 7(D) are exemplary of the raw eddy current signals 100 received by the data acquisition system. The analog signals often drift (off the horizontal axis). The signals from one scan direction are displaced 102 with respect to signals from the reverse scan direction. Signal noise is filtered out through the use of an analog filter that eliminates signals above 1200 Hz, in the preferred embodiment. Digitization of the signal is accomplished by an A/D convertor that samples and digitizes the analog signal.

The eddy current is separated into its in-phase and out-of-phase components by the phase detectors 90, 92.

These in-phase and out-of-phase signal components are applied to the vertical and horizontal channels 104, 106 in the data acquisition system for each probe. The in-phase signal component is most sensitive to lift-off changes in the distance between the probe and metal surface. The out-of-phase signal is less sensitive to lift-off and, thus, is generally more indicative of metal flaws and cracks. Nevertheless, both in- and out-of-phase signals are usually displayed or plotted.

The digitized eddy current signals are corrected for drift by using a linear least-square analysis fit of the data in step 1004. The least square curve formula used in the preferred embodiment is that shown in Table A:

TABLE A $E.C.L.S._i = mx_i + b$ where E.C.L.S. is the Eddy Current Least Square value for each sampled data point (i) of an eddy current signal having N sampled data points. The formulas for the variables m and b are as shown in Table B:

TABLE B $$m = \frac{\sum_{i=1}^{N} x_i y_i - N\bar{x}\bar{y}}{\sum_{i=1}^{N} x_i^2 - N\bar{x}}$$

$$b = \frac{\bar{x} \sum_{i=1}^{N} (x_i y_i) - \left(\sum_{i=1}^{N} x_i^2\right) \bar{y}}{N\bar{x}^2 - \sum_{i=1}^{N} x_i^2}$$

where x and y are the data coordinates, such as shown in FIGS. 7(A) to 7(D), for the individual sampled data points. Moreover, $\bar{x}$ and $\bar{y}$ are the mean values of all data coordinates.

In step 1006, the raw eddy current data points from each probe for each channel is subtracted from the corresponding E.C.L.S. value to determine the eddy current difference value for each sampled data point:

$EC\ Difference_i = EC\ signal_i - E.C.L.S._i$

Plotting the EC difference values removes drifting, tilting and offsets the eddy current data records.

The eddy current data from scans in one direction is offset from scans taken in the opposite direction. This displacement 102 results from mechanical backlash that occurs when the carriage reverses direction, and from time delays in signal response due to circuit amplifiers and filters in the signal processing circuits. The time delay due to filter response can be reduced, but not eliminated, by increasing the bandwidth of the output of the eddy current instrumentation.

To correct for the signal offsets due to reversing the scanning direction, a known metal crack is scanned to calibrate the instrument and data acquisition system. The displacement 102 between data taken from different directions over the known crack is measured in step 1008. The known crack is created by an electro-discharge machine (EDM) process.

The position of the known crack is set at a preselected location or precisely located with a measuring microscope. A calibration scan is made in one direction over the known crack with a conventional mechanical coordinate system to measure the true location of the known crack relative to an established reference, such as the end of the retaining ring. The relative position of the crack is also measured by scanning the eddy current probe in one direction and tracking the relative position of the probe where the eddy current signal is maximum with respect to the known crack. This relative distance is compared to the true distance between the reference and the crack. The difference between the relative and true distances is the offset (displacement) for that one scan direction. This same procedure is repeated for an eddy current scan in the opposite direction. In this manner the offsets to be applied to the scanning of the probe are measured.

In step 1010, the value of these measured displacements are divided by one-half and is then used to shift the data for scans in both directions. For example, data from scans in the positive direction are advanced by one-half of the displacement and data from scans in the negative direction are retarded by one-half of the displacement.

The data from each probe are normalized to a standard probe. The standard probe has been arbitrarily selected as probe No. 1. In step 1012, the data from the standard probe, e.g., probe 1, is multiplied by 1 because that data is already normalized by definition. To normalize the data from the other probes, the signal scale ratio between probe 1 (standard probe) and the other probes, e.g. probe 2, is calculated with respect the signal magnitude for a known (calibration) crack, in step 1014. This signal scale ratio is applied to the signal data for the respective probe, in step 1016. The signal scale ratio depends on each probe and is calculated for both channels (in- and out-of-phase) of signals. With the application of the scale ratio, the processed eddy current data from each probe are normalized, aligned, centered on the horizontal axis, and filtered. Next, the signals are collated to account for the interlaced scanning.

As shown in FIG. 8, the processed signals for both channels for all of the probes and all scans in both directions are arranged in spatial order in step 1020. In particular, the signals are received by the data acquisition system in the order of scanning. Because of interlaced scanning, the signals from the second rotation of the probe carriage are received after the signals from the first rotation around the retaining ring. The signals must be collated so that the signals from the second rotation of the carriage interlace with the signals from the first rotation. In this way, the signals can be plotted or displayed in spatial order to show the eddy current signals for the metal surface.

In step 1022, one or more threshold levels are applied to the eddy current signals to discriminate the data. The threshold levels are selected as being indicative of a given metal crack depth or "size" based upon calibrated data, in step 1024. The threshold is applied to the magnitude of the eddy current signal. In step 1025, data exceeding the threshold is compared to calibrated eddy current flaw values obtained in step 1028. Based on this comparison, the data is arranged into crack/flaw "size" information as a function of surface location. This size vs. location information can be displayed or plotted through the use of color codes or other highlighting means.

In step 1030, the eddy current data exceeding threshold levels, spatially adjacent eddy current data is analyzed to determine if it also exceeds the thresholds to ascertain the direction and length of material cracks and flaws. The number of adjacent data exceeding threshold values is determined and the mid-point of the data coordinates is calculated. Using these adjacent values, the centroid of the crack/flaw region and the extend of the region is calculated.

In addition, the regions of above-threshold crack data is given an identifying marker flag value and the coordinates of the region are written into a storage file with the marker flag. In steps 1032 and 1034, each flagged crack/flaw region is identified in a printed document listing the coordinates, size, and dimensional extent of each flaw/crack, and/or each region is displayed and color coded by depth and size for evaluation by an operator.

The eddy current display is a conventional device used to display eddy current probe data usually by means of an oscilloscope type display. It can be coupled to a strip chart or a computer controlled a CRT display or other color printout. The computer may be used to analyze the data from the eddy current probe.

While the invention has been described in its preferred embodiment, the invention is not limited to this disclosed embodiment. Rather, the invention covers various modifications and equivalent arrangements included within the spirit and scope the appended claims.

What is claimed is:

1. An apparatus for monitoring eddy currents comprising:
    a plurality of eddy current probes each having at least one current carrying coil for producing a signal indicative of electromagnetic eddy currents in an interior surface of a cylinder;
    a carriage on which said plurality of probes are mounted, said carriage holding said probes a substantially constant distance over said interior surface;
    translation means moving said carriage across said interior surface parallel to an axis of said cylinder such that said probes trace straight scan lines across said surface, said translation means comprising at least one shaft extending parallel to the cylinder axis in said cylinder and said carriage being slidably coupled to said shaft, said translation means rotating said carriage around said interior surface for at least two rotations, and with each rotation of said translation means interlacing the scan lines of said probes with scan lines from a previous rotation; and
    data acquisition means for processing said signals from said probes and interlacing said signals taken during said scan lines.

2. An apparatus as in claim 1 wherein said translation means further comprises a ring mounted inside of said cylinder and said shaft having one end movably attached to said ring perimeter.

3. An apparatus as in claim 2 wherein said ring perimeter includes gear teeth that engage a motorized block that circumnavigates said ring and said shaft extends perpendicularly from said block.

4. An apparatus as in claim 1 wherein said at least one shaft includes a rotating screw shaft engaged to said carriage and said carriage being moved by said rotation of said screw shaft.

5. A method for interlaced eddy current scanning of an interior surface of a cylinder using a plurality of eddy current probes mounted in a carriage, said method comprising the steps of:
    a. transversing the interior surface of the cylinder with the carriage to record eddy currents along a first set of scan lines separated by the distance between the probes in the carriage, b. again transversing the interior surface of the cylinder with the carriage to record eddy currents along a second set of scan lines separated by the distance between the probes in the carriage, the second set of scan lines interlaced with the first set of scan lines; and c. collating the records of eddy currents so that the records of the second set of scan lines interlace with the records of the first set of scan lines; and d. displaying information indicative of the collated records.

6. A method as in claim 5 wherein steps (a) and (b) further comprise traversing the carriage along straight scan lines parallel to an axis of the cylinder.

7. A method as in claim 5 further comprising step (e) in which the carriage is moved a circumferential distance equal to an integer multiple of the distance between scan lines and step (e) is performed between steps (a) and (b).

8. A method as in claim 5 wherein steps (a) and (b) are repeated until the carriage has at least once been moved around the inner circumference of the cylinder.

* * * * *